United States Patent
Pan

[19]

[11] Patent Number: 5,908,432
[45] Date of Patent: Jun. 1, 1999

[54] SCALPEL WITH RETRACTABLE BLADE

[76] Inventor: Huai C. Pan, 7330 Tamarron Pl., Westchester, Ohio 45069

[21] Appl. No.: 09/049,008

[22] Filed: Mar. 27, 1998

[51] Int. Cl.[6] .................................................. A61B 17/32
[52] U.S. Cl. .......................................... 606/167; 606/182
[58] Field of Search .................................... 606/167, 159, 606/182, 185

[56] References Cited

U.S. PATENT DOCUMENTS

| | | |
|---|---|---|
| D. 155,378 | 10/1949 | Beckstrom . |
| 4,802,476 | 2/1989 | Noerenberg et al. ............... 128/303.14 |
| 5,411,512 | 5/1995 | Abidin et al. ............................ 606/167 |
| 5,431,672 | 7/1995 | Cote et al. . |
| 5,531,754 | 7/1996 | Shackelford, Sr. et al. . |
| 5,545,175 | 8/1996 | Abidin et al. . |
| 5,569,281 | 10/1996 | Abidin et al. . |
| 5,599,351 | 2/1997 | Haber et al. . |
| 5,620,453 | 4/1997 | Nallakrishnan . |
| 5,620,454 | 4/1997 | Pierce et al. . |
| 5,665,099 | 9/1997 | Pilo et al. ................................ 606/167 |
| 5,730,751 | 3/1998 | Dillon et al. ............................ 606/167 |

FOREIGN PATENT DOCUMENTS

| | | |
|---|---|---|
| 651790 | 7/1994 | Australia . |
| 555196-A1 | 8/1993 | European Pat. Off. . |

*Primary Examiner*—Michael Buiz
*Attorney, Agent, or Firm*—Richard C. Litman

[57] ABSTRACT

A scalpel with a retractable blade comprising a handle having a proximal section grasped by the surgeon and a distal section, and a blade holder slidable in a channel defined in the distal section of the handle. The distal section has a hinged flap to provide access to the blade for removal and replacement of the blade when in the retracted position, and can accommodate disposable blades having a variety of sizes and shapes. The scalpel has an ergonomically shaped button mounted on the blade holder providing fingertip control over retraction and extension of the blade.

8 Claims, 5 Drawing Sheets

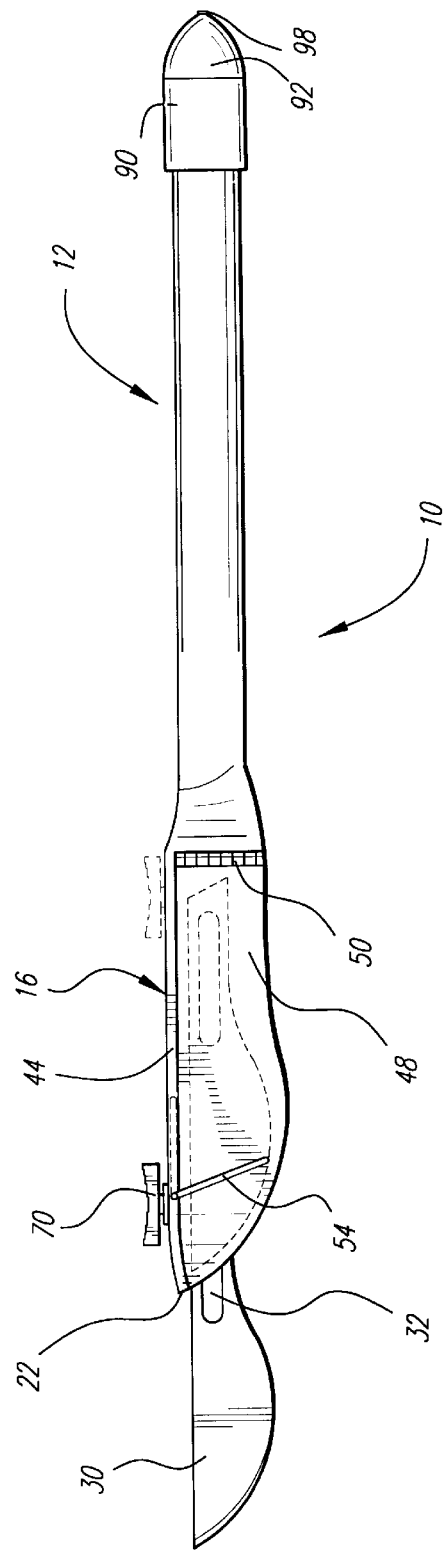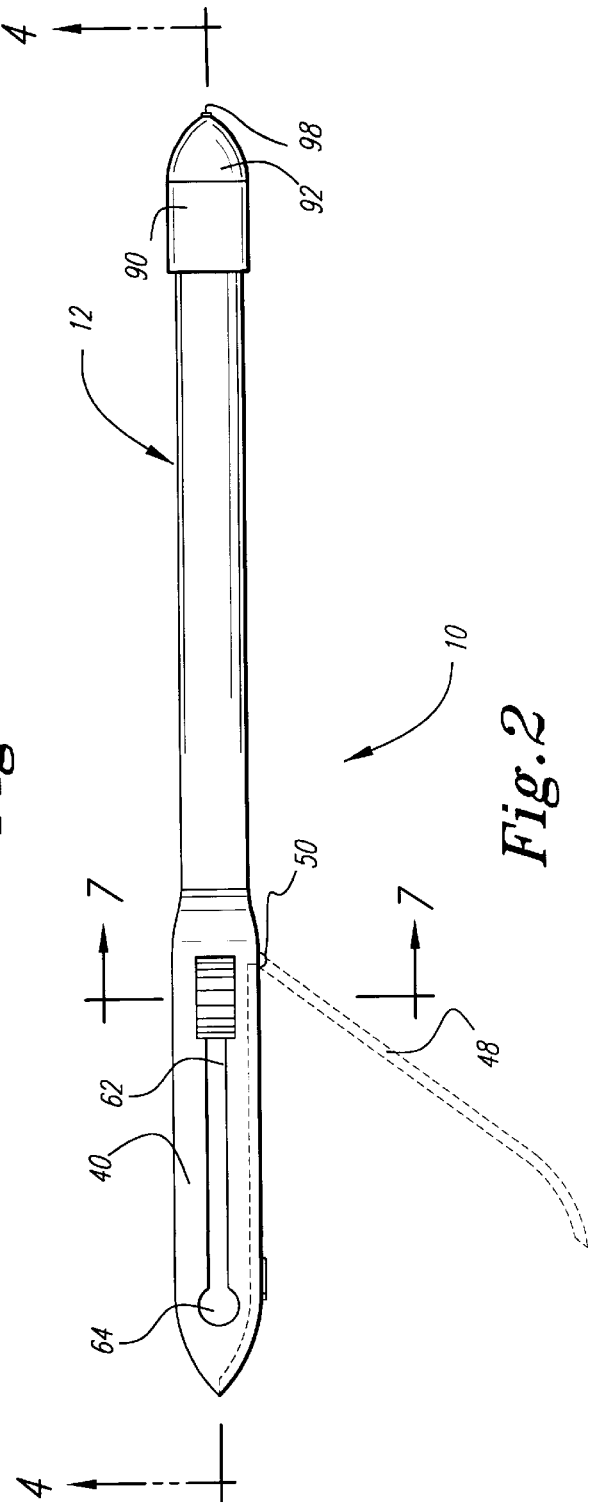

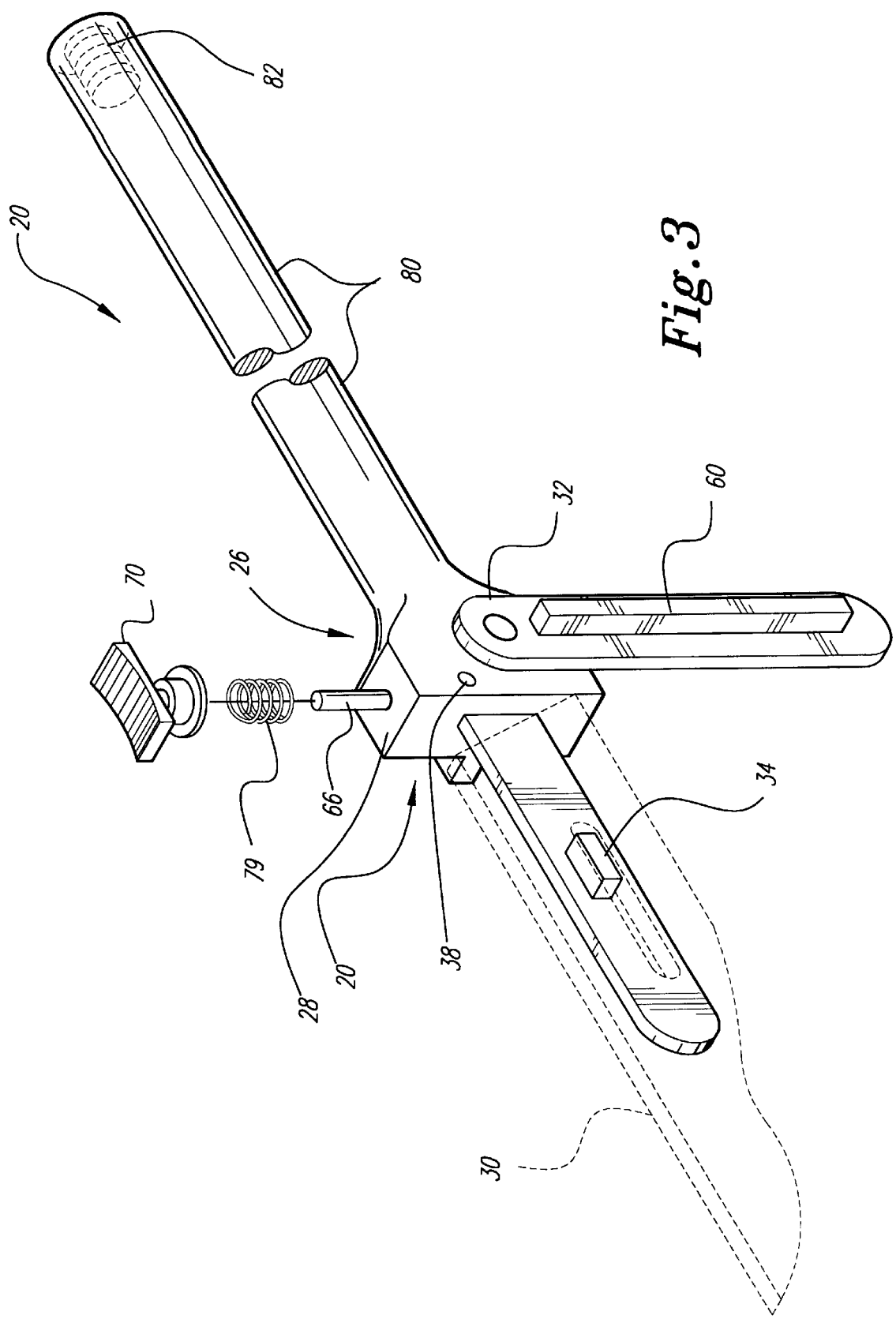

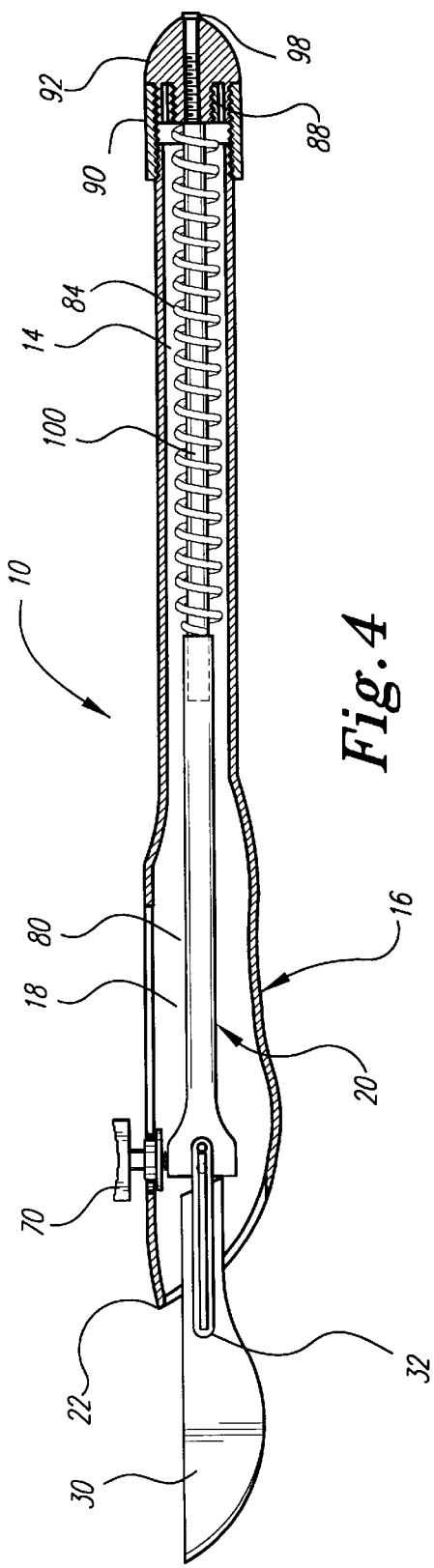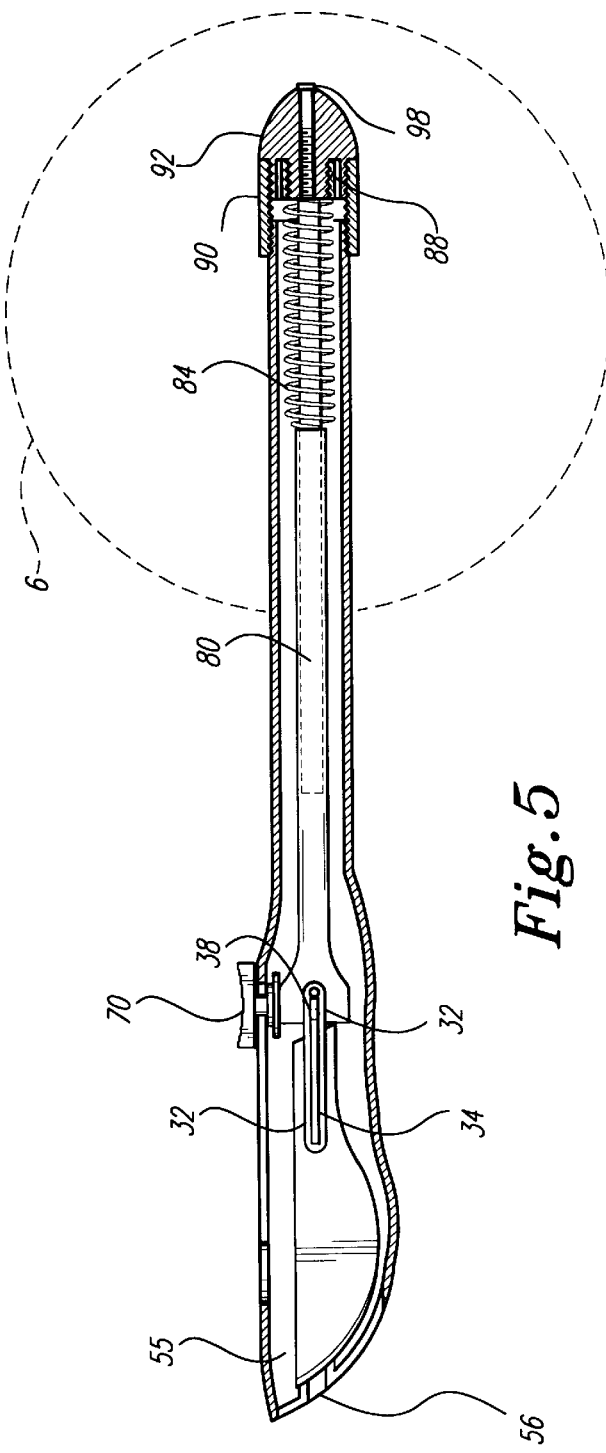

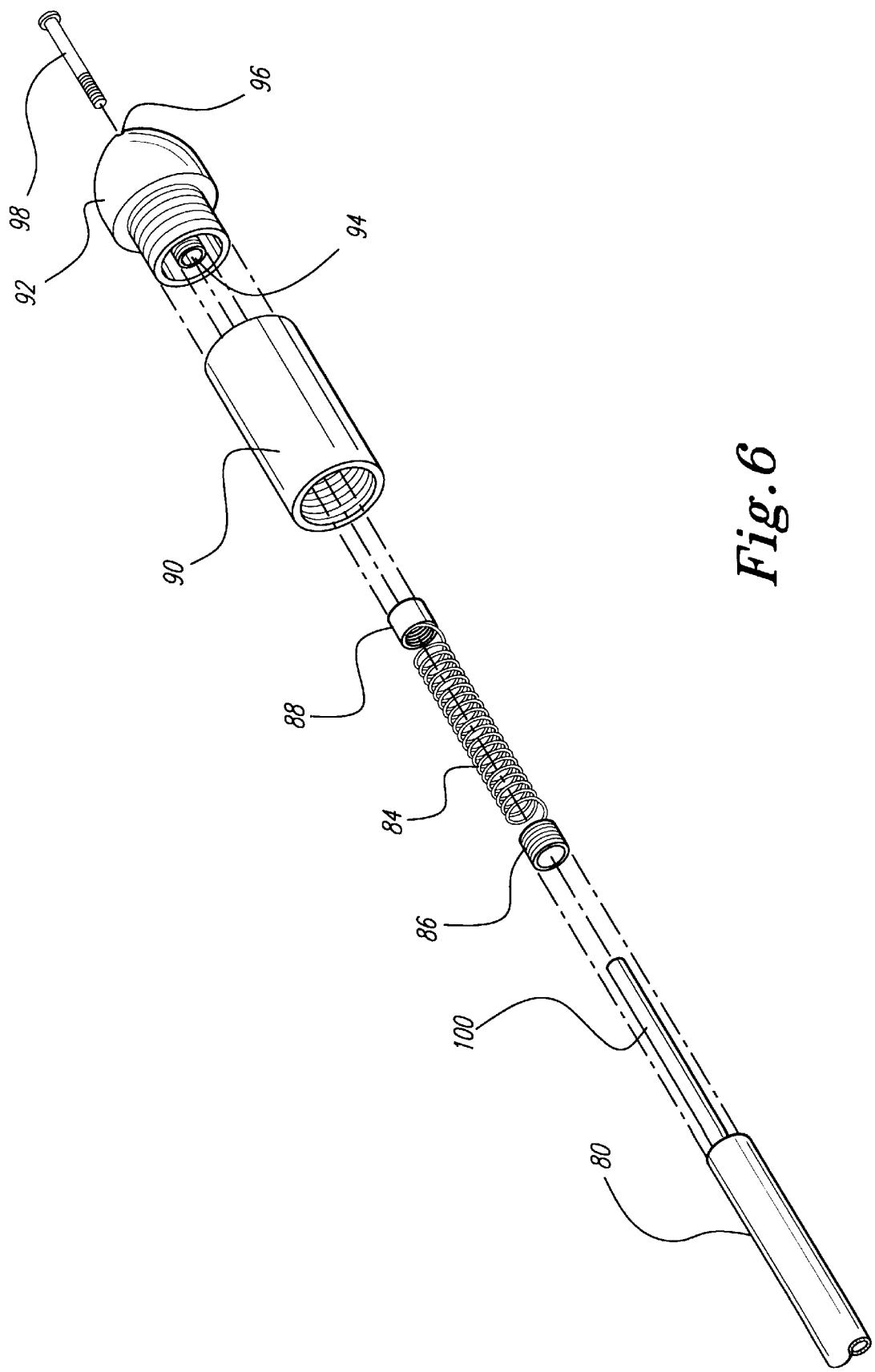

SCALPEL WITH RETRACTABLE BLADE

BACKGROUND OF THE INVENTION

1. Field of the Invention

The present invention relates to scalpels, and more particularly, to a scalpel handle and retractable blade holder for use with disposable or replaceable scalpel blades having a variety of sizes and cutting shapes.

2. Description of the Related Art

In the operating room surgical scalpels undergo frequent handling back and forth between members of the surgical team, often in circumstances where speed is a consideration. While there has always been a degree of concern over cuts and nicks which may accidentally occur in the course of such handling, fears over the transmission of AIDS and other infectious diseases through such open wounds have led to various devices for protecting operating room personnel such as retractable scalpel blades and retractable shields for fixed position scalpel blades.

The scalpel described in Cote (U.S. Pat. No. 5,431,672 issued Jul. 11, 1995) is a disposable scalpel in which the blade is mounted on a slidable carriage having an extended cutting position, an intermediate shielded position, and a fully retracted position in which the blade is locked inside the handle for disposal, the slide being controlled a button and slot on the side of the handle. Shackleford (U.S. Pat. No. 5,531,754 issued Jul. 2, 1996) describes a retractable blade mounted on a body member which slides in the handle, controlled by serrations on the body member extending through a slot on the bottom of the handle, with spring clips to lock the blade in place.

A guarded finger scalpel having spring arms which extend the blade when pressed between the thumb and forefinger is described in U.S. Pat. No. 5,545,175 issued to Abidin, et al. on Aug. 13, 1996. The blade does not lock in the cutting position. A surgical knife for ophthalmic surgery is described in U.S. Pat. No. 5,620,453, issued Apr. 15, 1997 to Nallakrisnan. The blade is extended to a cutting position by pressing a plunger at the end of the handle, and the depth of cut is adjustable by a micrometer. Four embodiments of a permanently retractable scalpel blade are described in U.S. Pat. No. 5,599,351 issued Feb. 4, 1997 to Haber et al. A scalpel with the blade mounted on a mandrel biased in a retracted position by a tension spring is described in Australian Patent 651,790 issued to Dillon, et al. Jul. 28, 1994.

Representative examples of a blade held in a fixed position with a retractable guard or shield sliding on the handle are described in U.S. Pat. No. 5,569,281 issued Oct. 29, 1996 to Abidin, et al., U.S. Pat. No. 5,620,454 issued Apr. 15, 1997 to Pierce, et al., and European Patent EP 555196 issued to Abidin. While not a scalpel, the sliding blade knife in U.S. Des. Pat. No. 155,378 shows a button and slot on top of the knife handle, but does not show a blade locking position.

None of the above inventions and patents, taken either singularly or in combination, is seen to describe a scalpel handle and blade holder adapted to receiving replacement scalpel blades in a variety of sizes, nor to have an ergonomic button design for controlling extension of the scalpel blade as shown in the instant invention. Thus a scalpel with a retractable blade solving the aforementioned problems is desired.

SUMMARY OF THE INVENTION

The invention comprises a handle for a surgical scalpel including a blade holder adapted to receiving disposable scalpel blades having a variety of sizes and cutting shapes. Disposable surgical blades come in a variety of sizes and shapes which are identified by number, and are designed for use with scalpel handles differing in size and weight and which are also identified by number. For example, a #10 blade has a rounded cutting edge and fits a #3, #7 or #9 handle, while #20, #21, and #22 blades have the same shape but are larger, fitting a #4 handle. A #11 blade has a straight edge coming to a sharp point, a #12 blade is shaped like a hook, a #15 blade is shaped like #10 but has a smaller and shorter cutting edge, all of these blades fitting a #3, #7 or #9 handle. A #23 blade has a curved cutting edge coming to more of a point than #20, #21 or #22, and fits a #4 handle. Currently most scalpels with retractable blades are designed so the blade is not replaceable. The scalpel handle of the present invention can be seen to comprise two sections, a proximal section grasped by the surgeon and a distal section shaped to form a protective sleeve which may accommodate blades having different sizes and shapes.

Accordingly, it is a principal object of the invention to provide a scalpel with a retractable blade having a protective sleeve which protects the surgeon and operating room personnel from nicks and cuts when the blade is in a retracted position, but which also accepts replaceable disposable surgical blades having a variety of sizes and shapes.

It is another object of the invention to provide a convenient and protected mode of replacing the surgical blade by providing the protective sleeve of the handle with a hinged flap with a latch means whereby the surgeon may access the surgical blade when it is retracted within the handle for removal and replacement.

It is a further object of the invention to provide an ergonomic means of retracting and extending the blade into the handle by providing a spring-biased button having a concave shape mounted on a blade holder slidable in a channel in the protective sleeve of the handle which provides fingertip control over extension and retraction of the scalpel blade.

It is an object of the invention to provide improved elements and arrangements thereof for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

FIG. 1 is a side view of a scalpel with a retractable blade shown with the blade extended according to the present invention.

FIG. 2 is a top view of a scalpel with a retractable blade according to the present invention.

FIG. 3 is a front perspective view of the blade holder.

FIG. 4 is a cross-sectional view taken along the line 4—4 of FIG. 2 with the blade extended.

FIG. 5 is the cross-sectional view of FIG. 4 with the blade retracted.

FIG. 6 is an enlarged view of the proximal portion of the scalpel with the parts exploded.

Similar reference characters denote corresponding features consistently throughout the attached drawings.

DETAILED DESCRIPTION OF THE PREFERRED EMBODIMENTS

Figure 8:
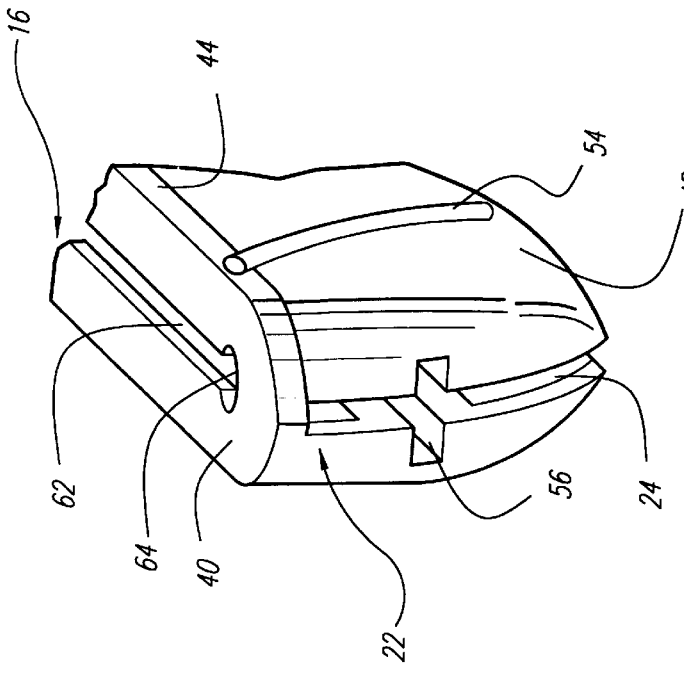
FIG. 8 is an end view of the scalpel of the present invention with the blade retracted.

The present invention describes a surgical scalpel with a retractable blade. More particularly, as shown in FIGS. 1 through 9, the invention comprises a handle 10 and a blade holder 20 designed for use with conventional disposable surgical blades 30 well known in the prior art.

As shown in FIGS. 1 and 5, the handle 10 includes a proximal section 12 having a proximal channel 14 defined therein and a distal section 16 having a distal channel 18 defined therein, the proximate channel 14 and the distal channel 18 being in communication with each other. The handle 10 also includes a distal end 22 having a slot 24, shown in FIG. 8, defined therein. Blade 30 extends through slot 24 in the cutting position.

The blade holder 20 is slidably disposed within the distal channel 18. The blade holder 20, shown more particularly in FIG. 3, includes a body 26 having a top surface 28 and mounting means for mounting a disposable scalpel blade 30 (not part of the invention) on the blade holder 20. Conventional disposable surgical blades generally are made with a standard sized and shaped slot defined in the side of the blade. In the preferred embodiment shown in FIG. 3, the mounting means is a pivoting blade retainer 32, a projection 34 from the vertical wall 36 of the blade holder 20, and a clasp 38 on the body of the blade holder 20 to lock the blade retainer 32 in place when a blade 30 is mounted on the projection 34. The projection 34 is sized to receive blades of varying sizes, including at least #10, #11, #12 and #15 in the preferred embodiment of the invention. Alternative embodiments of the invention may be made to accommodate larger size blades, such as #20 through #23, simply by making a proportionally larger distal section 16 and blade holder 20.

Figure 7:
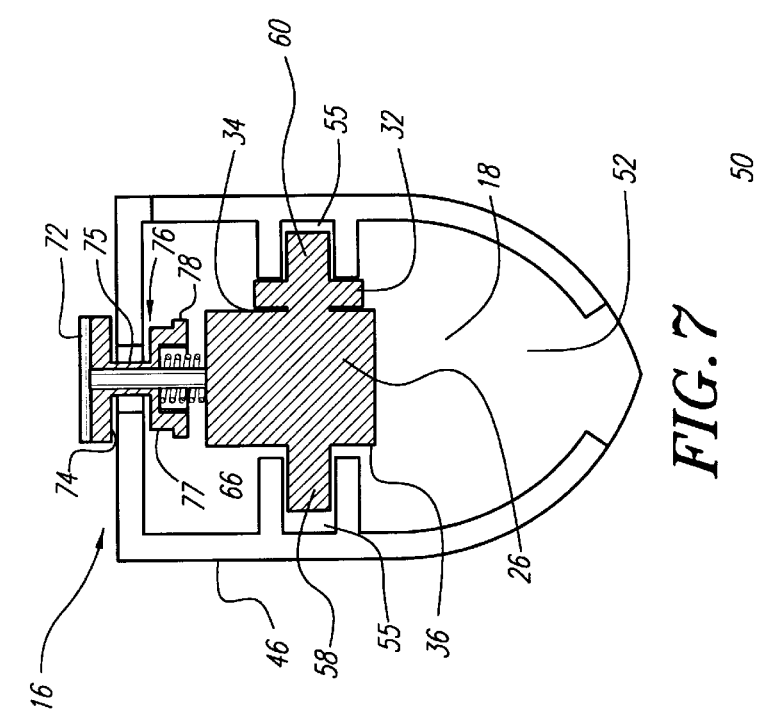
FIG. 7 is a cross-sectional view taken along the line 7—7 of FIG. 2.
Figure 9:
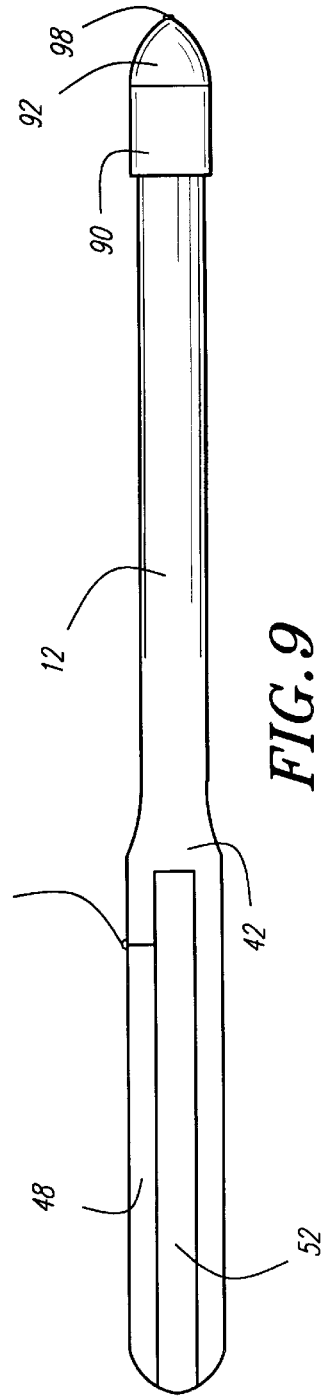
FIG. 9 is a bottom view of the scalpel with a retractable blade.

In the preferred embodiment as shown in FIGS. 7, 8, and 9, the distal section 16 of the handle 10 has substantially the shape of a parallelepiped, including a top surface 40, a bottom surface 42, a lateral surface 44 and a second lateral surface 46. The lateral surface 44 has a flap door 48 pivoting on a hinge 50, so that the flap door 48 pivots towards the proximate section 12 of the handle 10 in the open position. The flap door 48 and the second lateral surface 46 convexly converge downwards and define a slot 52 in the bottom surface 42 of the distal section 16 of the handle 10 in order to accommodate blades which have a good deal of curvature. The lateral surface 44 has a latch means 54, shown in FIG. 1, which has an open position to permit opening of the flap door 48 to gain access to the blade holder 20 to insert and remove blades 30 when the blade holder 20 is in a retracted position, and has a latched position in which the flap door 48 is latched in a closed position.

As best shown in FIGS. 7 and 8, the second lateral surface 46 and the flap door 48 each have an inner surface 55 with a longitudinal groove 56 defined therein. The blade holder 20 includes a flange 58 extending horizontally from one side of the vertical wall 36 and the blade retainer 32 also includes a flange 60 extending horizontally, the flanges 58 and 60 being slidably engaged in the grooves 56 defined in the flap door 48 and the second lateral surface 46.

The scalpel includes sliding means for sliding the blade holder 20 with the distal channel 18 of the handle 10. In the preferred embodiment as shown in FIG. 2, the top surface 40 of the distal section 16 of the handle 10 has a slot 62 defined therein extending longitudinally, with a circular aperture 64 defined in the top surface 40 at one end of the slot 62, the circular aperture 64 having a diameter greater than the width of the slot 62.

As shown in FIG. 3, the blade holder 20 has a pin 66 mounted vertically on the top surface 28 of the body 26, which pin 66 extends vertically through the slot 62 in the top surface 40 of the handle 10. As most clearly seen in FIG. 7, the handle 10 includes a button 70 having a top surface 72 and a bottom surface 74. The top surface 72 of the button 70 is concave upwards to easily conform to the shape of a fingertip. The top surface 72 may also be serrated to give better traction when the finger is enclosed in a rubber glove. The bottom surface 74 of the button 70 has a cylindrical stem 76 extending therefrom, the stem 76 being hollow and extending through the slot 62 and being aligned with the pin 66 of the blade holder 20. The stem 76 has a flange 78 at the end of the stem 76, so the button 70 may be engaged by the fingertip of the user, sliding the stem 76 through the slot 62 and thus sliding the blade holder 20 and the blade 30 between a cutting position and a retracted position, the stem 76 being retained in the slot 62 by the flange 78.

The handle 10 has a biasing means which retains the blade 30 in a normally retracted position in which the blade 30 is disposed entirely within the distal channel 18 of the handle 10. In the embodiment shown in FIGS. 5 and 6, the body of the blade holder 20 includes a cylinder 80 extending into the proximate channel 14 of the proximal section 12 of the handle 10. The cylinder 80 has a bore 82 defined therein, the bore 82 having internal screw threads. The handle 10 includes a tension spring 84. In the embodiment shown, the tension spring 84 is welded at one end to a barrel screw 86 which matingly threads into the bore 82 of the cylinder 80. The other end of the spring 84 is welded to barrel screw 88 which has internal threads.

The handle 10 has a hollow, cylindrical barrel 90 which screws into the proximal end of the handle 10, and an end cap 92 which screws into barrel 90. Barrel screw 88 is connected to end cap 92 by means of a threaded fitting 94 integral with end cap 92. End cap 92 has a bore 96 defined therein extending through threaded fitting 94. A pin screw 98 extends through bore 96, barrel screw 88, spring 84, barrel screw 86 and is screwed into a piston rod 100 having a bore 102 with internal threads defined therein. The piston rod 100 is slidably disposed within the bore 82 of the cylinder 80. Thus tension spring 84 is rigidly attached to end cap 92 at one end and the cylinder 80 of the blade holder 20 at the other end, the spring 84 tension normally acting as a bias means to keep the blade holder 20 retracted towards the proximate section 12 of the handle 10, thereby retaining blade 30 within the protective sheath of the distal channel 18 of the handle 10. Thus the spring 84 may be removed and replaced as needed.

The handle 10 includes locking means for retaining the blade 30 in a cutting position. The hollow stem 76 extending from the bottom surface 74 of button 70 has a top section 75 and a bottom section 77. The diameter of the top section 75 is sized to permit the top section 75 to slide within the slot 62. The bottom section 77 of stem 76 has a diameter greater than the width of slot 62 but small enough to freely slide vertically in the circular aperture 64 at the end of slot 62. The handle 10 includes a small helical compression spring 79 disposed within the hollow bottom section 77 of stem 76 and about pin 66 on the top surface 28 of the body 26 of blade holder 20. Thus the bottom section 77 of stem 76 is disposed in the distal channel 18 beneath slot 62 when the blade is in the retracted position, so that spring 79 is compressed.

When the user slides button 70 to the distal end of the handle 10 so that stem 76 is aligned with circular aperture 64, spring 79 extends vertically, pushing the bottom section 77 of the stem 76 through circular aperture 64, flange 78 retaining the base of stem 76 in distal channel 18, thereby locking blade 30 in the cutting position. The blade 30 may be retracted again by depressing button 70 to compress spring 79 until the bottom section 77 of stem 76 is again disposed within distal channel 18 and top section 75 is again slidable in slot 62, whereby tension spring 84 assists the user in pulling blade holder 20 back towards the retracted position.

In the preferred embodiment, the handle 10 and blade holder 20 are made of stainless steel or other autoclavable materials conventional in the art in order to be reusable. In the preferred embodiment, the proximate section 12 of the handle 10 has the shape of a right circular cylinder.

In operation, the latch 54 is pivoted upwards and the flap door 48 is pivoted towards the proximal section 12 of the handle 10 to the open position. The pivoting blade retainer 32 is freed from clasp 38 and the retainer 32 is pivoted downwards. A disposable blade 30 is inserted on projection 34 using a needle holder or hemostat. The retainer 32 is pivoted upwards, secured to clasp 38, the flap door 48 is closed and secured with latch 54. The blade 30 is maintained in a retracted position during handling.

When it is desired to make an incision, the button 70 is slid forward in slot 62 extending blade 30 through slot 24 until stem 76 is aligned in aperture 64, when spring 79 pushes the bottom section 77 through aperture 64 to lock blade 30 in the cutting position. After making any required incisions, button 70 is depressed until the top section 75 is aligned with slot 62 and the blade 30 is retracted into the distal channel 18 of handle 10, which acts as a protective sheath for the blade 30 during further handling. After use the blade 30 may be removed by reversing the above procedure and replaced or properly disposed of in a suitable container.

It is to be understood that the present invention is not limited to the embodiments described above, but encompasses any and all embodiments within the scope of the following claims. It will be apparent that tension spring 84 may be replaced with a compression spring if the circular aperture 64 is moved from the distal end of slot 62 to the proximal end of slot 62. However, this would bias blade 30 in the cutting position normally and require the blade 30 to be locked in the retracted position, which, for safety reasons, is not preferred.

It will also be apparent to those skilled in the art that considerable simplification in parts may be achieved if spring 84 is made nonremoveable. In that event one end of spring 84 may be rigidly attached to an interior wall extending transversely in the proximate section 12 of handle 10. Cylinder 80 might be replaced with a rod to which the other end of spring 84 is rigidly attached, with or without a stop means between the proximal 12 and distal 16 sections of handle 10 to limit the travel of the blade holder. With such an arrangement, end cap 92 need not be threaded, but may secure to the proximal end of the handle 10 by detents, in order to be removable and replaceable by a handle extension. Also, the proximal portion of the handle might then be rectangular in shape to suit the preference of the physician.

The essential advantages of the present invention, including an ergonomically shaped button 70 for retracting the blade 30 placed in a convenient location on the handle 10 not likely to be accidentally disturbed during use, a protective flap door 48 to maintain the blade 30 in a retracted position in the handle during insertion and removal of the blade 30, and the capacity to accommodate a range of conventional disposable blades through the mounting means and shape of the distal section 16 of the handle 10, can be achieved through various embodiments of the present invention.

I claim:

1. A scalpel with a retractable blade comprising:

a) a handle having a proximal section and a distal section, the proximal section having a proximal channel defined therein and the distal section having a distal channel defined therein, and a distal end having a slot defined therein, the distal section of said handle having substantially the shape of a parallelepiped, including a top surface, a bottom surface, a lateral surface, and a second lateral surface;

b) a blade holder slidably disposed within said distal channel, said blade holder having a body, the body having a top surface and including mounting means for mounting a disposable scalpel blade on said blade holder;

c) sliding means for sliding said blade holder in the distal channel of said handle;

d) biasing means for retaining the blade holder in a retracted position whereby the scalpel blade is disposed entirely within said distal channel;

e) a locking means for retaining the blade holder in a cutting position whereby the scalpel blade is extended through the slot in the distal end of said handle and locked in position; and f) access means for access to the scalpel blade when the blade holder is in the retracted position whereby the blade may be removed and replaced, said access means including a flap door pivotally hinged to the lateral surface of the distal section of said handle, said door having an open position and a closed position, said door and said second lateral surface being convex downwards and defining a slot in the bottom surface of said distal section.

2. The scalpel with a retractable blade according to claim 1, wherein said access means further comprises:

a) a latch means disposed on said lateral surface having an open position for moving said flap door to the open position and having a latched position for latching said flap door in the closed position; and b) wherein the flap door hinged to said lateral surface is disposed with relation to the mounting means of said blade holder in order to permit access for removal and insertion of the scalpel blade from and to said mounting means when said blade holder is in the retracted position.

3. The scalpel with a retractable blade according to claim 2, wherein:

a) the top surface of said distal section has a slot defined therein extending longitudinally, having a circular aperture at one end of said slot, the diameter of the circular aperture being greater than the width of said slot;

b) the lateral surface, the second lateral surface, and the flap door of said distal section each have an inner surface including a longitudinal groove defined in said inner surfaces;

c) said blade holder includes a vertical wall having a flange extending horizontally on one side of the vertical wall, and a pivoting blade retainer having a flange on the opposite side of the vertical wall, the flanges being slidably engaged in the grooves defined in the lateral surfaces and flap door of said distal section;

d) said sliding means comprises:

(i) a pin mounted vertically on the top surface of the body of said blade holder, said pin extending vertically through the slot in the top surface of said distal section;

(ii) a button having a top surface and a bottom surface, the top surface of said button being concave upwards;

(iii) a stem extending from the bottom surface of said button, said stem being hollow and extending through the slot in the top surface of said distal section, being aligned with the pin on the top surface of the body of said blade holder, said stem having a flange at the end of the stem, whereby the button and the stem slide in the slot of said distal section and are retained in the slot by the flange at the end of the stem.

4. The scalpel with a retractable blade according to claim 3, wherein:

(a) the hollow cylindrical stem extending from the bottom surface of said button has a top section and a bottom section, the top section being slidable within the slot defined in the top surface of said distal section, the bottom section having a diameter greater than the width of the slot defined in the top surface of said distal section and less than the diameter of the circular aperture; and (b) said locking means comprises a compression spring disposed within the hollow bottom section of said stem and about the pin on the top surface of said blade holder, whereby said bottom section is disposed in the distal channel so the spring is compressed when the blade is retracted, and whereby said spring extends vertically in order to push the bottom section of said stem through said circular aperture to lock the blade in a cutting position when the blade holder slides towards the distal end of the handle to align the bottom section with the circular aperture.

5. The scalpel with a retractable blade according to claim 4, wherein:

a) the height of said blade holder is greater than the diameter of the proximate channel of said proximate section;

b) said blade holder includes a cylinder extending into the proximate channel of said proximate channel, the cylinder having a bore defined therein;

c) said biasing means comprises a tension spring disposed within the proximal channel connected to the proximal section of said handle at one end of the spring and to the cylinder of said blade holder at the opposite end of said tension spring.

6. The scalpel with retractable blade according to claim 5, wherein said mounting means comprises the pivoting blade retainer of said blade holder, a projection from the vertical wall of said blade holder adapted to receive the slot of a disposable scalpel blade, and a clasp on the vertical wall of said blade holder, said blade retainer pivoting into contact with the projection from the vertical wall of said blade holder and locking in the clasp on the vertical wall of said blade holder in order to secure the disposable scalpel blade on said blade holder.

7. The scalpel with retractable blade holder according to claim 6 wherein the proximal section of said handle has the shape of a right circular cylinder.

8. The scalpel with retractable blade holder according to claim 7, further comprising a removable cap at the proximal end of said handle, whereby said tension spring may be removed and replaced.

* * * * *